(12) United States Patent
Brodbeck et al.

(10) Patent No.: US 6,747,049 B2
(45) Date of Patent: Jun. 8, 2004

(54) OXAZOLE DERIVATIVES

(75) Inventors: Bernd Brodbeck, Steinen-Hoellstein (DE); Hans Hilpert, Muenchenstein (CH); Roland Humm, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/611,139

(22) Filed: Jul. 1, 2003

(65) Prior Publication Data

US 2004/0006116 A1 Jan. 8, 2004

(30) Foreign Application Priority Data

Jul. 3, 2002 (EP) .............................. 02014828

(51) Int. Cl.$^7$ .................. A61K 31/421; A61P 3/10; C07D 263/32
(52) U.S. Cl. .................. 514/374; 548/235; 548/236
(58) Field of Search ................. 548/235, 236; 514/374

(56) References Cited

U.S. PATENT DOCUMENTS

| | | | |
|---|---|---|---|
| 4,011,326 | A | 3/1977 | Jensen |
| 5,089,514 | A | 2/1992 | Hulin |
| 5,599,826 | A | 2/1997 | Mertens et al. |
| 5,856,529 | A | 1/1999 | Catt et al. |
| 6,121,397 | A | 9/2000 | MacLeod et al. |
| 6,291,685 | B1 | 9/2001 | Junghans et al. |
| 6,441,185 | B2 | 8/2002 | Kühnle et al. |

FOREIGN PATENT DOCUMENTS

| | | |
|---|---|---|
| EP | 0903343 | 3/1999 |
| EP | 1 078 923 | 2/2001 |
| WO | WO 91/19702 | 12/1991 |
| WO | WO 94/13650 | 6/1994 |
| WO | WO 95/17394 | 6/1995 |
| WO | WO 97/25042 | 7/1997 |
| WO | WO 99/08501 | 2/1999 |
| WO | WO 99/10339 | 3/1999 |
| WO | WO 00 08002 | 2/2000 |
| WO | WO 02 16331 | 2/2002 |

OTHER PUBLICATIONS

Gustavsson et al, *Chemical Abststracts*, vol 138, No. 106,504 (2003).*
Haigh et al., Tetrahedron: Asymmetry, 10, pp. 1353–1367 (1999).
Gotteland et al., Synlett., 9, pp. 931–932 (1995).
Hulin et al., J. Med. Chem., 39, pp. 3897–3907 (1996).
Nicolaou et al., J. Am. Chem. Soc., 122, pp. 3830–3838 (2000).
Nichols et al., Anal. Biochem., 257, pp. 112–119 (1998).
Einsiedel et al., Bioorg. Med. Chem. Lett., 10, pp. 2041–2044 (2000).
Goto et al., Chem. Pharm. Bull., 19, pp. 2050–2057 (1971).
Reichstein et al., Helvetica Chimica Acta, 16, pp. 121–129 (1933).
Diels et al., Chem. Ber., 48, pp. 897–905 (1915).
Wightman et al., J. Org. Chem., 43, pp. 2167–2170 (1978).
Musser et al., J. Med. Chem., 30, pp. 62–67 (1987).
Rahman et al., J. Chem. Soc. Perkin Trans. 1, 12, pp. 2973–2977 (1983).
Kelly et al., J. Am. Chem. Soc., 110, pp. 6471–6480 (1988).
Kneen et al., Synthetic Communications, 16, pp. 1635–1640 (1986).
Kim et al., Can. J. Chem., 60, pp. 2093–2098 (1982).
Párkányi et al., Monatsh. Chem., 123, pp. 637–645 (1992).
McDougald et al., Current Biology, 5, pp. 618–621 (1995).
Keller et al., Trends Endocrin. Metab., 4, pp. 291–296 (1993).
Malamas, M.S. et al., Eur. J. Med. Chem., vol. 36, No. 1, pp. 31–42 (2001).
Hulin B. et al., Current Pharmaceutical Design, vol. 2 pp. 85–102 (1996).
Oplinger, et al., ACS National Meeting, San Diego, Apr. 1–5, 2001, Poster 238, Division of Medicinal Chemistry, Section C.
STN International® CAPLUS Database, Accession No. 2000: 117035; Collins et al WO 2000008002.

\* cited by examiner

Primary Examiner—Robert W. Ramsuer
(74) Attorney, Agent, or Firm—George W. Johnston; Dennis P. Tramaloni; Eileen M. Ebel

(57) ABSTRACT

Compounds of formula I are provided

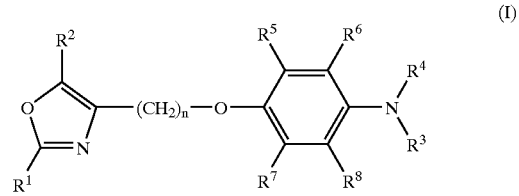

as well as pharmaceutically acceptable salts and esters thereof, wherein $R^1$ to $R^3$ and n have the significance given in the specification can be used to treat non-insulin dependent diabetes mellitus.

17 Claims, No Drawings

OXAZOLE DERIVATIVES

BACKGROUND OF THE INVENTION

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ (also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80–90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease syndrome. Among the comorbidities associated with T2D are for example insulin resistance, dyslipidemia, hypertension, endothelial dysfunction and inflammatory atherosclerosis.

Current first line treatment for diabetes generally involves low fat—and glucose—diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives who had been approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i.e. with an improved lipid profile effect on top of the normalization of glucose- and insulin-levels (Keller and Wahli: Trends Endocrin. Metab. 1993; 4:291–296, Macdonald and Lane: Current Biology Vol.5 pp.618–621 (1995)).

SUMMARY OF THE INVENTION

The invention provides compounds of formula I

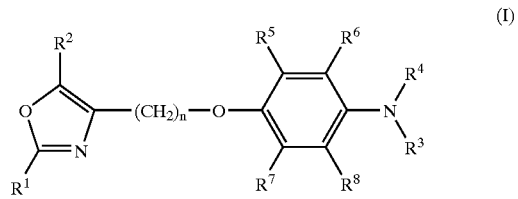

and pharmaceutically acceptable salts and esters thereof, wherein $R^1$ is aryl;

$R^2$ is hydrogen, alkyl or cycloalkyl;

$R^3$ is hydrogen, alkyl, aralkyl, aryl, alkylcarbonyl, arylcarbonyl, alkyl-$S(O)_2$— or aryl-$S(O)_2$—;

$R^4$ is aralkyl;

$R^5$, $R^6$, $R^7$ and $R^8$ are independently selected from hydrogen, alkyl or cycloalkyl; and n is 1, 2, 3, 4 or 5.

The compounds of formula I and their pharmaceutically acceptable salts and esters are insulin sensitizers, particularly PPAR activators.

DETAILED DESCRIPTION OF THE INVENTION

The present invention is concerned with oxazole derivatives useful as insulin sensitizers, particularly PPAR activators.

The invention provides compounds of formula I

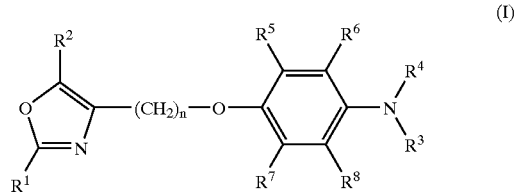

and pharmaceutically acceptable salts and esters thereof, wherein $R^1$ is aryl;

$R^2$ is hydrogen, alkyl or cycloalkyl;

$R^3$ is hydrogen, alkyl, aralkyl, aryl, alkylcarbonyl, arylcarbonyl, alkyl-$S(O)_2$— or aryl-$S(O)_2$—;

$R^4$ is aralkyl;

$R^5$, $R^6$, $R^7$ and $R^8$ are independently selected from hydrogen, alkyl or cycloalkyl; and n is 1, 2, 3, 4 or 5.

The compounds of formula I and their pharmaceutically acceptable salts and esters are insulin sensitizers, particularly PPAR activators.

The compounds of the present invention bind to and activate both PPARα and PPARγ, simultaneously and very efficiently. Therefore, these compounds combine the antiglycemic effect of PPARγ activation with the antidyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential.

Accordingly, the compounds of formula I can be used in the prophylaxis and/or treatment of diabetes, particularly non-insulin dependent diabetes mellitus, elevated blood pressure, increased lipid and cholesterol levels, atherosclerotic diseases or metabolic syndrome.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxy preferably methoxy and ethoxy, and most preferred methoxy.

The term "aryloxy", alone or in combination, signifies a group of the formula aryl-O— in which the term "aryl" has the previously given significance, such as phenyloxy.

The term "aryl", alone or in combination, signifies a phenyl or naphthyl group, preferably a phenyl group which optionally carries one or more substituents each independently selected from halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, or nitro. Examples of aryl include phenyl, chlorophenyl, trifluoromethylphenyl, chlorofluorophenyl, aminophenyl, methylcarbonylphenyl, methoxyphenyl, methylendioxyphenyl, 1-naphthyl and 2-naphthyl. Preferred is phenyl, 3-chlorophenyl, 3-trifluoromethylphenyl, 3-aminophenyl, 4-methylcarbonylphenyl, 4-methoxyphenyl and particularly phenyl.

The term "aralkyl", alone or in combination, signifies an alkyl or cycloalkyl group as previously defined in which one or more, preferably one hydrogen atom has been replaced by an aryl group as previously defined. Preferred are benzyl, benzyl substituted with hydroxy, alkoxy or halogen, preferably fluorine. Particularly preferred is benzyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two substituents together with the nitrogen to which they are bound forming a ring. Typical amino groups are, for example, —$NH_2$, methylamino, ethylamino, dimethylamino, diethylamino, methylethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine.

The term "carbonyl", alone or in combination signifies the —C(O)— group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123.

Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Preferred are compounds of formula I, wherein $R^1$ is phenyl.

A preferred embodiment of the present invention are compounds of formula I, wherein $R^2$ is alkyl, preferably methyl.

Also preferred are compounds of formula I, wherein $R^3$ is alkyl, aralkyl, aryl, alkylcarbonyl, arylcarbonyl, alkyl-S(O)$_2$— or aryl-S(O)$_2$—. Further preferred are those compounds, wherein $R^3$ is methyl, propyl, benzyl, methylcarbonyl, phenylcarbonyl, methyl-S(O)$_2$—, phenyl-S(O)$_2$—, phenyl or phenyl substituted with one or more, preferably one or two substituents independently selected from alkyl, halogen, trifluoromethyl and alkoxy.

A further preferred aspect of the present invention are compounds of formula I, wherein $R^3$ is alkyl or phenyl, wherein phenyl is optionally mono- or disubstituted with halogen. Particularly preferred are those compounds of formula I, wherein $R^3$ is propyl, phenyl, fluorophenyl or difluorophenyl.

Further preferred compounds of formula I are those, wherein $R^4$ is arylmethyl. Particularly preferred are the compounds of formula I, wherein $R^4$ is benzyl substituted with carboxy and optionally further substituted with fluoro, chloro, trifluoromethyl or alkoxy.

Also preferred are compounds according to formula I, wherein $R^5$ is hydrogen.

Further preferred are compounds according to formula I, wherein $R^6$ is hydrogen.

Another preferred aspect of the present invention are compounds of formula I, wherein $R^7$ is hydrogen.

Also preferred are compounds according to formula I, wherein $R^8$ is hydrogen.

Particularly preferred compounds according to formula I are those, wherein $R^5$, $R^6$, $R^7$ and $R^8$ are hydrogen.

Another preferred embodiment of the present invention are the compounds of formula I, wherein n is 1, 2 or 3. Particularly preferred compounds of formula I are these, wherein n is 2.

Examples of preferred compounds of formula (I) are 1. 2-[(Acetyl-{4-[2-(5-methyl-2-phenyl-oxazol-4-yl)-ethoxy]-phenyl}-amino)-methyl]-benzoic acid;
2. 2-[(Benzoyl-{4-[2-(5-methyl-2-phenyl-oxazol-4-yl)-ethoxy]-phenyl}-amino)-methyl]-benzoic acid;
3. 2-[(Methanesulfonyl-{4-[2-(5-methyl-2-phenyl-oxazol-4-yl)-ethoxy]-phenyl}-amino)-methyl]-benzoic acid;
4. 2-[(Benzenesulfonyl-{4-[2-(5-methyl-2-phenyl-oxazol-4-yl)-ethoxy]-phenyl}-amino)-methyl]-benzoic acid;
5. 2-[(Methyl-{4-[2-(5-methyl-2-phenyl-oxazol-4-yl)-ethoxy]-phenyl}-amino)-methyl]-benzoic acid;
6. 2-[({4-[2-(5-Methyl-2-phenyl-oxazol-4-yl)-ethoxy]-phenyl}-propyl-amino)-methyl]-benzoic acid;
7. 2-[(Benzyl-{4-[2-(5-methyl-2-phenyl-oxazol-4-yl)-ethoxy]-phenyl}-amino)-methyl]-benzoic acid;
8. 2-[({4-[2-(5-Methyl-2-phenyl-oxazol-4-yl)-ethoxy]-phenyl}-o-tolyl-amino)-methyl]-benzoic acid;
9. 2-[((3-Fluoro-phenyl)-{4-[2-(5-methyl-2-phenyl-oxazol-4-yl)-ethoxy]-phenyl}-amino)-methyl]-benzoic acid;
10. 2-[({4-[2-(5-Methyl-2-phenyl-oxazol-4-yl)-ethoxy]-phenyl}-m-tolyl-amino)-methyl]-benzoic acid;
11. 2-{[{4-[2-(5-Methyl-2-phenyl-oxazol-4-yl)-ethoxy]-phenyl}-(3-trifluoromethyl-phenyl)-amino]-methyl}-benzoic acid;
12. 2-[((4-Fluoro-phenyl)-{4-[2-(5-methyl-2-phenyl-oxazol-4-yl)-ethoxy]-phenyl}-amino)-methyl]-benzoic acid;
13. 2-[({4-[2-(5-Methyl-2-phenyl-oxazol-4-yl)-ethoxy]-phenyl}-p-tolyl-amino)-methyl]-benzoic acid;
14. 2-[((4-Methoxy-phenyl)-{4-[2-(5-methyl-2-phenyl-oxazol-4-yl)-ethoxy]-phenyl}-amino)-methyl]-benzoic acid;
15. 2-[((3,4-Dimethyl-phenyl)-{4-[2-(5-methyl-2-phenyl-oxazol-4-yl)-ethoxy]-phenyl}-amino)-methyl]-benzoic acid;
16. 2-[((3,4-Difluoro-phenyl)-{4-[2-(5-methyl-2-phenyl-oxazol-4-yl)-ethoxy]-phenyl}-amino)-methyl]-benzoic acid;
17. 2-[((4-Fluoro-3-methyl-phenyl)-{4-[2-(5-methyl-2-phenyl-oxazol-4-yl)-ethoxy]-phenyl}-amino)-methyl]-benzoic acid;
18. 3-Fluoro-2-[({4-[2-(5-methyl-2-phenyl-oxazol-4-yl)-ethoxy]-phenyl}-phenyl-amino)-methyl]-benzoic acid;
19. 3-Chloro-2-[({4-[2-(5-methyl-2-phenyl-oxazol-4-yl)-ethoxy]-phenyl}-phenyl-amino)-methyl]-benzoic acid;

20. 2-[({4-[2-(5-Methyl-2-phenyl-oxazol-4-yl)-ethoxy]-phenyl}-phenyl-amino)-methyl]-3-trifluoromethyl-benzoic acid;
21. 3-Methoxy-2-[({4-[2-(5-methyl-2-phenyl-oxazol-4-yl)-ethoxy]-phenyl}-phenyl-amino)-methyl]-benzoic acid;
22. 4-Chloro-2-[({4-[2-(5-methyl-2-phenyl-oxazol-4-yl)-ethoxyl]-phenyl}-phenyl-amino)-methyl]-benzoic acid;
23. 4-Methoxy-2-[({4-[2-(5-methyl-2-phenyl-oxazol-4-yl)-ethoxy]-phenyl}-phenyl-amino)-methyl]-benzoic acid;
24. 5-Fluoro-2-[({4-[2-(5-methyl-2-phenyl-oxazol-4-yl)-ethoxy]-phenyl}-phenyl-amino)-methyl]-benzoic acid;
25. 2-[({4-[2-(5-Methyl-2-phenyl-oxazol-4-yl)-ethoxy]-phenyl}-phenyl-amino)-methyl]-benzoic acid; and
26. 2-Methoxy-6-[({4-[2-(5-methyl-2-phenyl-oxazol-4-yl)-ethoxy]-phenyl}-phenyl-amino)-methyl]-benzoic acid.

Examples of particularly preferred compounds of formula (I) are

2-[({4-[2-(5-Methyl-2-phenyl-oxazol-4-yl)-ethoxy]-phenyl}-phenyl-amino)-methyl]-benzoic acid;
2-[({4-[2-(5-Methyl-2-phenyl-oxazol-4-yl)-ethoxy]-phenyl}-propyl-amino)-methyl]-benzoic acid;
2-[((3-Fluoro-phenyl)-{4-[2-(5-methyl-2-phenyl-oxazol-4-yl)-ethoxy]-phenyl}-amino)-methyl]-benzoic acid;
2-[((3,4-Difluoro-phenyl)-{4-[2-(5-methyl-2-phenyl-oxazol-4-yl)-ethoxy]-phenyl}-amino)-methyl]-benzoic acid;
3-Fluoro-2-[({4-[2-(5-methyl-2-phenyl-oxazol-4-yl)-ethoxy]-phenyl}-phenyl-amino)-methyl]-benzoic acid; and
5-Fluoro-2-[({4-[2-(5-methyl-2-phenyl-oxazol-4-yl)-ethoxy]-phenyl}-phenyl-amino)-methyl]-benzoic acid.

The substituents and indices used in the following description of the processes have the significance given above unless indicated to the contrary.

Compounds of general formula I, wherein $R^1$, $R^2$, $R^4$ to $R^8$ and n are as previously defined and, wherein $R^3$ is hydrogen, alkyl, aralkyl, aryl, alkylcarbonyl, arylcarbonyl, alkyl-S(O)$_2$— or aryl-S(O)$_2$— can be prepared according to Scheme I and II:

Scheme I

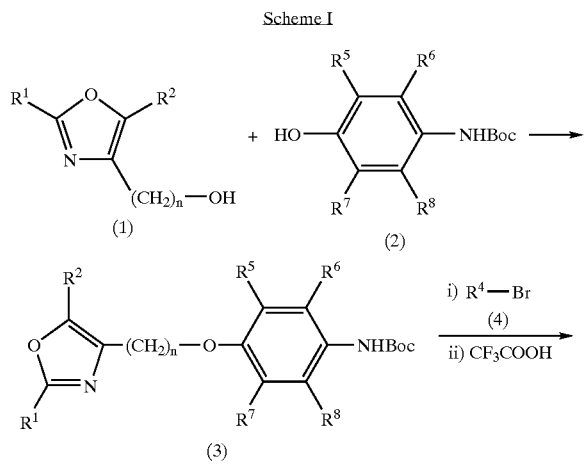

Boc means tert-butoxycarbonyl

The oxazolether (3) can be prepared by coupling of the alcohol (1) and the monoprotected aniline (2) under Mitsunobu conditions in THF (O. Mitsunobu, Synthesis, 1, 1981). Alkylation of (3) with (4) can be accomplished with KOH in DMSO followed by deprotection of the Boc group using CF$_3$COOH to give compound (5).

Scheme II

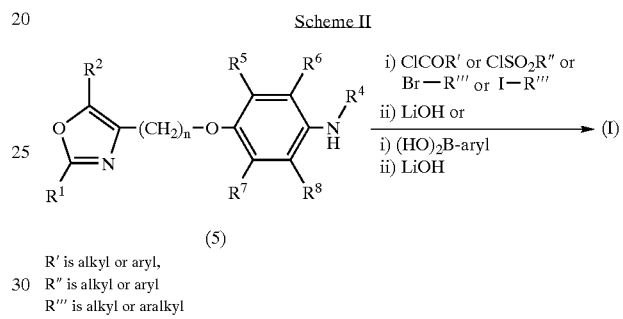

R' is alkyl or aryl,
R'' is alkyl or aryl
R''' is alkyl or aralkyl

Acylations and sulfonylations of the amine (5) can be carried out with the corresponding chlorides. Alkylations of (5) require preferably the corresponding alkyl iodids or benzyl bromide. All reactions can be performed in the presence of a base, e.g. NEt$_3$ in THF to give the precursor of (I) as the esters. In a second step the esters can be hydrolyzed with LiOH in a solvent mixture of THF, MeOH and water affording the target compounds (I). Arylations of the amine (5) can be performed with the corresponding boronic acids according to the method of Lam (P. Y. S. Lam, G. Vincent, C. G. Clark, S. Deudon, P. K. Jadhav, Tetrahedron Lett. 42, 3415, 2001) to give the precursor of (I) as the esters which can be hydrolyzed as described above.

In case a free carboxy group is present e.g. in substituent $R^4$ this carboxy group can be protected by methods known in the art e.g. as ethyl ester. Present OH residues can be protected using appropriate protecting groups such as e.g. as ethyl ester.

Alternatively, compounds of general formula I, wherein $R^1$, $R^2$, $R^4$ to $R^8$ and n are as previously defined and, wherein $R^3$ is hydrogen, alkyl, aralkyl, aryl, alkylcarbonyl, arylcarbonyl, alkyl-S(O)$_2$— or aryl-S(O)$_2$— can be prepared according to Scheme III:

Scheme III

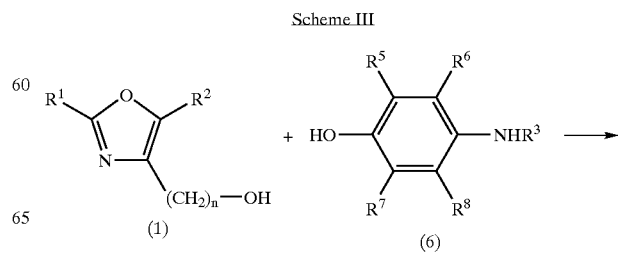

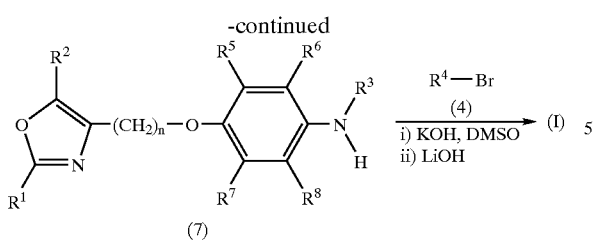

The alternative preparation of (I) according to Scheme III preferentially used when $R^3$ is fixed and $R^4$ is varied follows the same type of reactions as described in Schemes I and II.

In case a free carboxy group is present e.g. in substituent $R^4$ this carboxy group can be protected by methods known in the art e.g. as ethyl ester Starting compound (I) can be obtained e.g. according to Scheme IV or V:

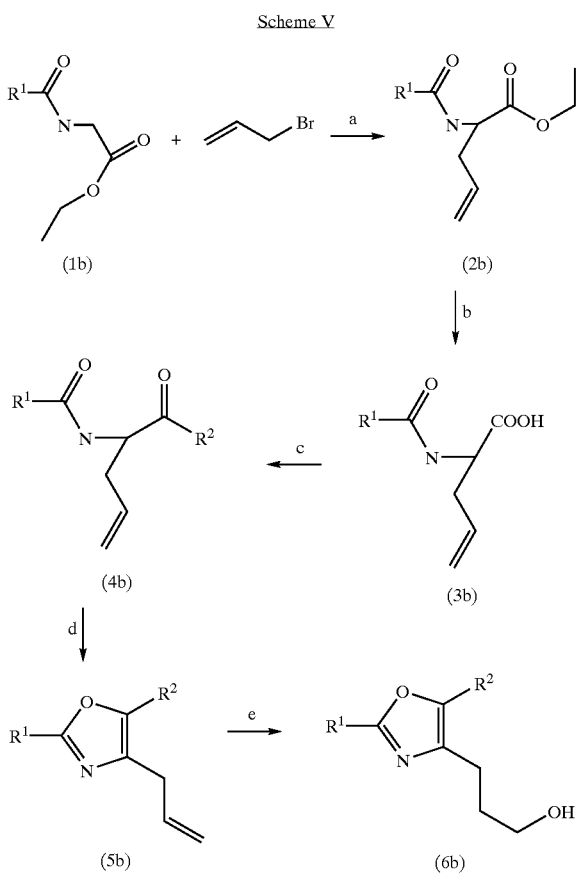

Aldehydes (1a) are commercially available or known. They are condensed with diketo-monoximes (2a) according to literature precedence (Goto, Y.; Yamazaki, M.; Hamana, M.; Chem Pharm Bull (1971), 19, 2050) in the presence of a strong acid, typically HCl, in a polar solvent like AcOH to yield the oxazole-N-oxides (3a) (step a). Subsequent treatment with $POCl_3$ in dichloromethane under reflux provides the corresponding primary chlorides (4a) (Goto, Y.; Yamazaki, M.; Hamana, M.; Chem Pharm Bull (1971), 19, 2050, step b). These intermediates are either used as such, transformed according to well established methods into the corresponding alcohols or activated alcohols like mesylates or tosylates or into the bromides or iodides, or finally further elaborated via $S_N2$-reaction with NaCN to give, via nitrils 5 (step c), exhaustive hydrolysis (step d) and reduction (step e), e.g. with borane in tetrahydrofuran, the building blocks (7a).

4-Chloromethyl-2-aryl or 2-heteroaryl-oxazoles (4a) with $R^2$ equal hydrogen are preferably prepared from the corresponding aryl or heteroaryl carboxamides and 1,3-dichloroacetone as described e.g. in Bioorg. Med. Chem. Lett. (2000), 10(17), 2041–2044.

Compounds of formula (I), wherein n is 1 can be obtained by reacting a compound of formula 4a with a compound of formula 6 analogous to the reactions shown in Scheme III.

N-Acyl-glycine esters (1b) are either commercially available, known, or can be prepared by standard operations of N-acylation. Mono-allylated esters (2b) can easily be obtained by double deprotonation of (1b) with a strong, non-nucleophilic base like LiHMDS in an aprotic solvent like THF, typically at −78° C., followed by treatment with allyl bromide to produce selectively the C-alkylated products (2b) (step a). Standard hydrolysis generates intermediate acids (3b) (step b), which are then transformed, following well established literature precedence (J. Med. Chem. (1996), 39, 3897), into compounds (4b) (step c). Ring-closure to the oxazole using trifluoro-acetic acid and trifluoro-acetic anhydride as reagents generates key intermediates (5b) (step d), which, finally, are elaborated via hydroboration to the target alcohols (6b), e.g. with 9-BBN in THF and ensuing oxidative work-up with $H_2O_2$ and NaOH (step e).

Starting compounds of formula (1), wherein n is 4 can be obtained as follows:

1) mesylation of a compound according to formula (6b)
2) SN2-reaction with NaCN in order to obtain the corresponding nitril
3) hydrolysis of the nitril
4) reduction e.g. with borane Starting compounds of formula (1), wherein n is 5 can be obtained as follows:

1) mesylation of a compound according to formula 1, wherein n is 4

2) SN2-reaction with NaCN in order to obtain the corresponding nitril
3) hydrolysis of the nitril
4) reduction e.g. with borane Starting compounds (2) and (6) are known or can be synthesized by methods known in the art, e.g. by nitration of the phenole using sulfuric- and salpetric-acid followed by reduction of the corresponding nitro phenole using catalytic hydrogenation or iron in hydrochloric acid. Boc protection of the primary amine can be accomplished with Boc anhydride in pyridine to give (2) or, alternatively, the unprotected aniline can be converted to compound (6) using the arylation procedure developed by Lam (P. Y. S. Lam, G. Vincent, C. G. Clark, S. Deudon, P. K. Jadhav, Tetrahedron Lett. 42, 3415, 2001).

Compounds according to formula (4) and the corresponding protected analogs can be prepared as follows: The substituted tolyl carbonic acid is protected as the ester using well known procedures, e.g. esterification with an alcohol and hydrochloric acid.

Bromination of the methyl group follows also well established procedures, e.g. using N-bromo succinimide and a catalytic amount of dibenzoyl peroxide in an halogenated solvent such as $CCl_4$.

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-l-yloxytris(dimethylamino)phosphonium hexafluorophosphate (BOP) or N,N-dicylohexylcarbodiimide (DCCI) to produce the carboxylic ester or carboxylic amide.

Further preferred is a process for the preparation of a compound according to formula I comprising one of the following reactions:

a) reaction of a compound according to formula (5)

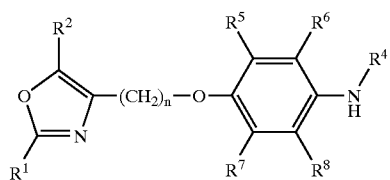

(5)

in the presence of $R^3$-Hal and following reaction in the presence of a hydroxide, preferably LiOH, in order to obtain a compound of formula I, wherein Hal means chlorine, bromine or iodine and $R^1$ to $R^8$ and n are defined as before. Particularly preferred is the above reaction, wherein $R^3$ means alkylcarbonyl or arylcarbonyl and Hal means chlorine. Further preferred is the above reaction, wherein $R^3$ means alkyl or aralkyl and Hal means bromine or iodine.

b) reaction of a compound according to formula (5) in the presence of $(HO)_2$B-aryl and following reaction in the presence of a hydroxide, preferably LiOH, in order to obtain a compound of formula I, wherein $R^1$, $R^2$, $R^4$ to $R^8$ and n are defined as before;

c) reaction of a compound according to formula (7)

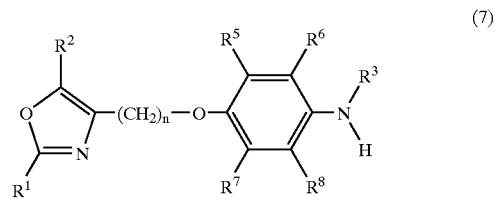

(7)

in the presence of $R^4$-Hal and following reaction in the presence of a hydroxide, preferably LiOH, in order to obtain a compound of formula I, wherein Hal means chlorine, bromine or iodine and $R^1$ to $R^8$ and n are defined as before. Preferred is the above reaction, wherein Hal means bromine.

Preferred intermediates are:

{4-[2-(5-Methyl-2-phenyl-oxazol-4-yl)-ethoxy]-phenyl}-carbamic acid tert-butyl ester
2-[(tert-Butoxycarbonyl-{4-[2-(5-methyl-2-phenyl-oxazol-4-yl)-ethoxy]-phenyl}-amino)-methyl]-benzoic acid ethyl ester
2-({4-[2-(5-Methyl-2-phenyl-oxazol-4-yl)-ethoxy]-phenylamino}-methyl)-benzoic acid ethyl ester and
{4-[2-(5-Methyl-2-phenyl-oxazol-4-yl)-ethoxy]-phenyl}-phenyl-amine.

The compounds of formula I described above for use as therapeutically active substances are a further object of the invention. Preferred is the use as therapeutically active substances for the prophylaxis and/or therapy of diabetes, non-insulin dependent diabetes mellitus, elevated blood pressure, increased lipid and cholesterol levels, atherosclerotic diseases or metabolic syndrome and particularly preferred non-insulin dependent diabetes mellitus.

Also an object of the invention are compounds described above for the preparation of medicaments for the prophylaxis and/or therapy of diseases which are modulated by PPARα and/or PPARγ agonists, preferably for the production of medicaments for the prophylaxis and/or therapy of diabetes, non-insulin dependent diabetes mellitus, elevated blood pressure, increased lipid and cholesterol levels, atherosclerotic diseases or metabolic syndrome and particularly preferred non-insulin dependent diabetes mellitus.

Likewise an object of the invention are pharmaceutical compositions comprising a compound of formula I described above and a therapeutically inert carrier. Another object of the present invention is the above pharmaceutical composition further comprising a therapeutically effective amount of a lipase inhibitor particularly, wherein the lipase inhibitor is orlistat.

An object of the invention is also the use of the compounds described above for the production of medicaments, particularly for the treatment and/or prophylaxis of diseases which are modulated by PPARα and/or PPARγ agonists, preferably diabetes, non-insulin dependent diabetes mellitus, elevated blood pressure, increased lipid and cholesterol levels, atherosclerotic diseases or metabolic syndrome and particularly preferred non-insulin dependent diabetes mellitus.

A further object of the present invention is the use of a compound of formula I in the manufacture of a medicament for the treatment and/or prophylaxis of diseases which are modulated by PPARα and/or PPARγ agonists in a patient who is also receiving treatment with a lipase inhibitor. Preferred is the above use, wherein the lipase inhibitor is orlistat. Particularly preferred is the above use for the treatment and/or prophylaxis of diseases, wherein the diseases are diabetes, non-insulin dependent diabetes mellitus, elevated blood pressure, increased lipid and cholesterol levels, atherosclerotic diseases or metabolic syndrome and particularly preferred non-insulin dependent diabetes mellitus.

A further object of the invention comprises compounds which are manufactured according to one of the described processes.

A further object of the invention is a method for the treatment and/or prophylaxis of diseases which are modulated by PPARα and/or PPARγ agonists, preferably diabetes, non-insulin dependent diabetes mellitus, elevated blood pressure, increased lipid and cholesterol levels, atherosclerotic diseases or metabolic syndrome and particularly preferred non-insulin dependent diabetes mellitus, whereby an effective amount of a compound of formula I is administered. Another object of the present invention is the above method which further comprises administration to the human a therapeutically effective amount of a lipase inhibitor, particularly, wherein the lipase inhibitor is orlistat. The above method for simultaneous, separate or sequential administration is also an object of the present invention.

Assay Procedures

The following tests can be used in order to determine the activity of the compounds of formula I.

Background information on the performed assays can be found in: Nichols J S et al. "Development of a scintillation proximity assay for peroxisome proliferator-activated receptor gamma ligand binding domain", (1998) Anal. Biochem. 257:112–119.

Full-length cDNA clones for human PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in E. coli strain BL21 (pLysS) cells by standard methods (Ref: Current Protocols in Molecular Biology, Wiley Press, edited by Ausubel et al.).

Radioligand Binding Assay

PPARα receptor binding was assayed in TKE10 (10 mM Tris-HCl, pH 8, 50 mM KCl, 2 mM EDTA, 0.1 mg/ml fatty acid free BSA and 10 mM DTT). For each 96 well 2.4 ug equivalent of GST-PPARα-LBD fusion protein and radioligand, e.g. 40000 dpm 2(S)-(2-benzoyl-phenylamino)-3-{4-[1,1-ditritio-2-(5-methyl-2-phenyl-oxazol-4-yl)-ethoxy]-phenyl}-propionic acid, were incubated in 100 ul volume at RT for 2 hrs. Bound ligand was removed from unbound ligand by solid phase separation using MultiScreen plates (Millipore) filled with 80 ul of SG25 according to the manufacturer's recommendations.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%O2:5%CO$_2$ atmosphere. Cells were seeded in 6 well plates at a density of $10^5$ Cells/well and then batch-transfected with either the pFA-PPARγ-LBD or pFA-PPARα-LBD expression plasmids plus the pFR-luc reporter plasmid and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final. 0.1% DMSO). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The compounds of the present invention exhibit IC$_{50}$ values of 0.1 nM to 50 μM, preferably 1 nM to 10 μM, particularly 1–3500 nM, more preferred 1 to 500 nM, for PPARα and PPARγ. The compounds further exhibit EC$_{50}$ values of 0.1 nM to 50 μM, preferably 1 nM to 10 μM, more preferably 1 to 3500 nM, particularly 1 to 500 nM, for PPARα and PPARγ.

| | PPARγ IC$_{50}$ (μM) | PPARα EC$_{50}$ (μM) | PPARγ EC$_{50}$ (μM) |
| --- | --- | --- | --- |
| Example 6 | 0.93 | 2.70 | 1.32 |
| Example 12 | 1.08 | 2.59 | 2.32 |
| Example 18 | 0.24 | 10 | 1.98 |
| Example 26 | 0.98 | 2.05 | 1.41 |
| Rosiglitazone | 0.465 | inactive | 0.025 |

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.5–500 mg, preferably 0.5–100 mg, of a compound of formula I.

The following Examples serve to illustrate the present invention in more detail. They are, however, not intended to limit its scope in any manner.

EXAMPLES

Preparation of the Starting Material of Examples 1–17 a) {4-[2-(5-Methyl-2-phenyl-oxazol-4-yl)-ethoxy]-phenyl}-carbamic acid tert-butyl ester To a solution of 5.00 g of (4-hydroxy-phenyl)-carbamic acid tert-butyl ester, 7.28 g of 2-(5-methyl-2-phenyl-1,3-oxazol-4-yl)ethan-1-ol and 9.40 g of triphenylphosphine in 100 ml of THF was added at 0° C. a solution of 7.25 g of diisopropyl azodicarboxylate in 50 ml of THF over 30 min and stirring was continued at 22° C. for 16 h. A further portion of 1.88 g of triphenylphosphine and 1.45 g of diisopropyl azodicarboxylate in 10 ml of THF was added at 0° C. and stirring was continued at 22° C. for 2 h after which time conversion was complete. The mixture was evaporated and the residue purified by chromatography ($SiO_2$, n-hexane/AcOEt 4:1) to give 7.5 g of the title compound as a colorless solid. MS: $(M+H)^-$ 395.4.

b) 2-[(tert-Butoxycarbonyl-{4-[2-(5-methyl-2-phenyl-oxazol-4-yl)-ethoxy]-phenyl}-amino)-methyl]-benzoic acid ethyl ester To a suspension of 3.41 g of powdered KOH in 110 ml of DMSO was added at 22° C. 6.00 g of {4-[2-(5-methyl-2-phenyl-oxazol-4-yl)-ethoxy]-phenyl}-carbamic acid tert-butyl ester and the suspension was stirred for 25 min. A solution of 7.40 g of 2-bromomethyl-benzoic acid ethyl ester in 10 ml of DMSO was added slowly keeping the temperature at 15–20° C. and stirring was continued at 22° C. for 2.5 h. The dark mixture was partitioned between 500 ml of a saturated aqueous $NH_4Cl$ and 200 ml of AcOEt, the organic layer was washed with saturated aqueous $NH_4Cl$ and water, dried and evaporated. The residue was purified by chromatography ($SiO_2$, n-hexane/AcOEt 4:1) to give 7.96 g of the title compound as a pale yellow oil. MS: $(M+H)^+$ 557.3.

c) 2-({4-[2-(5-Methyl-2-phenyl-oxazol-4-yl)-ethoxy]-phenylamino}-methyl)-benzoic acid ethyl ester To a solution of 7.00 g of 2-[(tert-butoxycarbonyl-{4-[2-(5-methyl-2-phenyl-oxazol-4-yl)-ethoxy]-phenyl}-amino)-methyl]-benzoic acid ethyl ester in 40 ml of dichloromethane was added 9.6 ml of trifluoroacetic acid and stirring was continued at 22° C. for 2.5 h. The mixture was partitioned between aqueous saturated $Na_2CO_3$ and dichloromethane, the organic layer was dried and evaporated. The residue was purified by chromatography ($SiO_2$, n-hexane/AcOEt 4:1) to give 3.14 g of the title compound as a pale yellow oil. MS: $(M+H)^+$ 457.5.

General Description for the Preparation of Examples 1–7

To a solution of 0.2 mmol of 2-({4-[2-(5-methyl-2-phenyl-oxazol-4-yl)-ethoxy]-phenylamino}-methyl)-benzoic acid ethyl ester prepared as described above and 0.4 mmol of triethylamine in 2 ml of THF was added 0.22 mmol of the corresponding acyl chloride or sulfo chloride or 0.22–2 mmol of the alkyl iodide or benzyl bromide followed by addition of a catalytic amount of dimethylamino pyridine in cases of slow conversions. The reaction mixtures were stirred at 22–55° C. until completion of the conversion. The suspension was filtered, the filtrate evaporated and the residue purified by preparative HPLC chromatography (RP-18, $CH_3CN/H_2O$ gradient) to give the product as the ester.

The esters (0.1 mmol) were hydrolyzed with 0.3 mmol of $LiOH.H_2O$ in 1 ml of THF, 0.5 ml of MeOH and 0.5 ml of water followed by purification using preparative HPLC chromatography (RP-18, $CH_3CN/H_2O$ gradient).

Example 1

2-[(Acetyl-{4-[2-(5-methyl-2-phenyl-oxazol-4-yl)-ethoxy]-phenyl}-amino)-methyl]-benzoic acid ethyl ester was obtained in 66% yield as a pale yellow gum. MS: $(M+H)^+$ 499.3. After hydrolysis, 2-[(acetyl-{4-[2-(5-methyl-2-phenyl-oxazol-4-yl)-ethoxy]-phenyl}-amino)-methyl]-benzoic acid was obtained in 61% yield as a white solid. MS: (M−H) 469.2.

Example 2

2-[(Benzoyl-{4-[2-(5-methyl-2-phenyl-oxazol-4-yl)-ethoxy]-phenyl}-amino-methyl]-benzoic acid ethyl ester was obtained in 65% yield as a colorless gum. MS: $(M+H)^+$ 561.4. After hydrolysis, 2-[(benzoyl-{4-[2-(5-methyl-2-phenyl-oxazol-4-yl)-ethoxy]-phenyl}-amino)-methyl]-benzoic acid was obtained in 71% yield as a white solid. MS: (M−H) 531.1.

Example 3

2-[(Methanesulfonyl-{4-[2-(5-methyl-2-phenyl-oxazol-4-yl)-ethoxy]-phenyl}-amino)-methyl]-benzoic acid ethyl ester was obtained in 57% yield as a yellow gum. MS:

(M+H)+ 535.3. After hydrolysis, 2-[(methanesulfonyl-{4-[2-(5-methyl-2-phenyl-oxazol-4-yl)-ethoxy]-phenyl}-amino)-methyl]-benzoic acid was obtained in 75% yield as a white solid. MS: (M–H) 505.2.

Example 4

2-[(Benzenesulfonyl-{4-[2-(5-methyl-2-phenyl-oxazol-4-yl)-ethoxy]-phenyl}-amino)-methyl]-benzoic acid ethyl ester was obtained in 89% yield as a pale yellow gum. MS: (M+H)− 597.1. After hydrolysis, 2-[(benzenesulfonyl-{4-[2-(5-methyl-2-phenyl-oxazol-4-yl)-ethoxy]-phenyl}-amino)-methyl]-benzoic acid was obtained in 66% yield as a white solid. MS: (M–H) 567.1.

Example 5

2-[(Methyl-{4-[2-(5-methyl-2-phenyl-oxazol-4-yl)-ethoxy]-phenyl}-amino)-methyl]-benzoic acid ethyl ester was obtained in 29% yield as a pale brown gum. MS: (M+H)− 471.1. After hydrolysis, 2-[(methyl-{4-[2-(5-methyl-2-phenyl-oxazol-4-yl)-ethoxy]-phenyl}-amino)-methyl]-benzoic acid was obtained in 64% yield as a pale yellow gum. MS: (M+H)+ 443.4.

Example 6

2-[({4-[2-(5-Methyl-2-phenyl-oxazol-4-yl)-ethoxy]-phenyl}-propyl-amino)-methyl]-benzoic acid ethyl ester was obtained in 59% yield as a yellow gum. MS: (M+H)+ 499.3. After hydrolysis, 2-[({4-[2-(5-methyl-2-phenyl-oxazol-4-yl)-ethoxy]-phenyl}-propyl-amino)-methyl]-benzoic acid was obtained in 83% yield as a pale yellow gum. MS: (M+H)+ 471.3.

Example 7

2-[(Benzyl-{4-[2-(5-methyl-2-phenyl-oxazol-4-yl)-ethoxy]-phenyl}-amino)-methyl]-benzoic acid ethyl ester was obtained in 55% yield as a pale yellow gum. MS: (M+H)+ 547.2. After hydrolysis, 2-[(benzyl-[4-[2-(5-methyl-2-phenyl-oxazol-4-yl)-ethoxy]-phenyl}-amino)-methyl]-benzoic acid was obtained in 59% yield as a pale yellow gum. MS: (M+H)+ 519.3.

General Description for the Preparation of Examples 8–17

According to the method described by P. Y. S. Lam et al., Tetrahedron Letters 42, 3415, 2001, a suspension of 0.44 mmol of the corresponding boronic acid and 0.25 g of molecular sieves in 3 ml of dichloromethane was treated subsequently with 0.22 mmol of 2-({4-[2-(5-methyl-2-phenyl-oxazol-4-yl)-ethoxy]-phenylamino}-methyl)-benzoic acid ethyl ester prepared as described above, 0.22 mmol of copper(II)acetate, 0.24 mmol of 2,2,6,6-tetramethylpiperidine-1-oxyl (TEMPO) and 0.44 mmol of NEt₃ and the mixture was stirred at 22° C. without sealing the flask (oxygen required) for 16 h. The mixture was filtered over a short pad of silica and the filtrate was purified by preparative HPLC chromatography (RP-18, CH₃CN/H₂O gradient) to give the product as the ester. The ester was hydrolyzed as described above.

Example 8

2-[({4-[2-(5-Methyl-2-phenyl-oxazol-4-yl)-ethoxy]-phenyl}-o-tolyl-amino)-methyl]-benzoic acid ethyl ester was obtained in 22% yield as a brown gum. MS: (M+H)+ 547.3. After hydrolysis, 2-[({4-[2-(5-methyl-2-phenyl-oxazol-4-yl)-ethoxy]-phenyl}-o-tolyl-amino)-methyl]-benzoic acid was obtained in 78% yield as a pale yellow gum. MS: (M+H)+ 519.3.

Example 9

2-[((3-Fluoro-phenyl)-{4-[2-(5-methyl-2-phenyl-oxazol-4-yl)-ethoxy]-phenyl}-amino)-methyl]-benzoic acid ethyl ester was obtained in 22% yield as a pale yellow gum. MS: (M+H)+ 551.1. After hydrolysis, 2-[((3-fluoro-phenyl)-{4-[2-(5-methyl-2-phenyl-oxazol-4-yl)-ethoxy]-phenyl}-amino)-methyl]-benzoic acid was obtained in 29% yield as a pale yellow gum. MS: (M+H)+ 523.2.

Example 10

2-[({4-[2-(5-Methyl-2-phenyl-oxazol-4-yl)-ethoxy]-phenyl}-m-tolyl-amino)-methyl]-benzoic acid ethyl ester was obtained in 33% yield as a pale yellow gum. MS: (M+H)+ 547.2. After hydrolysis, 2-[({4-[2-(5-methyl-2-phenyl-oxazol-4-yl)-ethoxy]-phenyl}-m-tolyl-amino)-methyl]-benzoic acid was obtained in 43% yield as a pale yellow gum. MS: (M+H)+ 519.3.

Example 11

2-{[{4-[2-(5-Methyl-2-phenyl-oxazol-4-yl)-ethoxy]-phenyl}-(3-trifluomethyl-phenyl)-amino]-methyl}-benzoic acid ethyl ester was obtained in 19% yield as a pale yellow gum. MS: (M+H)+ 601.1. After hydrolysis, 2-{[{4-[2-(5-methyl-2-phenyl-oxazol-4-yl)-ethoxy]-phenyl}-(3-trifluoromethyl-phenyl)-amino]-methyl}-benzoic acid was obtained in 31% yield as a pale yellow gum. MS: (M+H)+ 573.1.

Example 12

2-[((4-Fluoro-phenyl)-{4-[2-(5-methyl-2-phenyl-oxazol-4-yl)-ethoxy]-phenyl}-amino)-methyl]-benzoic acid ethyl ester was obtained in 17% yield as a pale yellow gum. MS: (M+H)+ 551.3. After hydrolysis, 2-[((4-fluoro-phenyl)-{4-[2-(5-methyl-2-phenyl-oxazol-4-yl)-ethoxy]-phenyl}-amino)-methyl]-benzoic acid was obtained in 70% yield as a pale yellow gum. MS: (M+H)+ 523.2.

Example 13

2-[({4-[2-(5-Methyl-2-phenyl-oxazol-4-yl)-ethoxy]-phenyl}-p-tolyl-amino)-methyl]-benzoic acid ethyl ester was obtained in 31% yield as a pale yellow gum. MS: (M+H)+ 547.2. After hydrolysis, 2-[({4-[2-(5-methyl-2-phenyl-oxazol-4-yl)-ethoxy]-phenyl}-p-tolyl-amino)-methyl]-benzoic acid was obtained in 81% yield as a pale yellow gum. MS: (M+H)+ 519.2.

Example 14

2-[((4-Methoxy-phenyl)-{4-[2-(5-methyl-2-phenyl-oxazol-4-yl)-ethoxy]-phenyl]-amino)-methyl]-benzoic acid ethyl ester was obtained in 37% yield as a pale yellow gum. MS: (M+H)+ 563.4. After hydrolysis, 2-[((4-methoxy-phenyl)-[4-[2-(5-methyl-2-phenyl-oxazol-4-yl)-ethoxy]-phenyl}-amino)-methyl]-benzoic acid was obtained in 43% yield as a pale yellow gum. MS: (M+H)+ 535.3.

Example 15

2-[((3,4-Dimethyl-phenyl)-{4-[2-(5-methyl-2-phenyl-oxazol-4-yl)-ethoxy]-phenyl}-amino)-methyl]-benzoic acid ethyl ester was obtained in 31% yield as a pale yellow gum. MS: (M+H)+ 561.4. After hydrolysis, 2-[((3,4-dimethyl-phenyl)-{4-[2-(5-methyl-2-phenyl-oxazol-4-yl)-ethoxy]-phenyl}-amino)-methyl]-benzoic acid was obtained in 12% yield as a pale yellow gum. MS: (M+H)+ 533.3.

Example 16

2-[((3,4-Difluoro-phenyl)-{4-[2-(5-methyl-2-phenyl-oxazol-4-yl)-ethoxy]-phenyl}-amino)-methyl]-benzoic acid ethyl ester was obtained in 9% yield as a pale yellow gum. MS: (M+H)+ 569.2. After hydrolysis, 2-[((3,4-difluoro-phenyl)-{4-[2-(5-methyl-2-phenyl-oxazol-4-yl)-ethoxy]-phenyl}-amino)-methyl]-benzoic acid was obtained in 57% yield as a pale yellow gum. MS: (M+H)+ 541.2.

Example 17

2-[((4-Fluoro-3-methyl-phenyl)-{4-[2-(5-methyl-2-phenyl-oxazol-4-yl)-ethoxy]-phenyl}-amino)-methyl]-benzoic acid ethyl ester was obtained in 10% yield as a yellow gum. MS: (M+H)+ 565.4. After hydrolysis, 2-[((4-fluoro-3-methyl-phenyl)-{4-[2-(5-methyl-2-phenyl-oxazol-4-yl)-ethoxy]-phenyl}-amino)-methyl]-benzoic acid was obtained in 39% yield as a white solid. MS: (M+H)+ 537.5.

Preparation of the Starting Material of Examples 18–26

{4-[2-(5-Methyl-2-phenyl-oxazol-4-yl)-ethoxy]-phenyl}-phenyl-amine

To a solution of 0.50 g 4-hydrox-phenylaniline, 0.83 g of 2-(5-methyl-2-phenyl-1,3-oxazol-4-yl)ethan-1-ol and 1.06 g of triphenylphosphine in 20 ml of THF was added at 0° C. a solution of 0.82 g of diisopropyl azodicarboxylate in 10 ml of THF over 30 min and stirring was continued at 22° C. for 5 h. The mixture was evaporated and the residue purified by chromatography (SiO$_2$, n-hexane/AcOEt 6:1) to give 0.62 g of the title compound as a colorless solid. MS: (M+H)+ 371.4.

General Description for the Preparation of Examples 18–26

To a suspension of 0.76 mmol of powdered KOH in 2.5 ml of DMSO was added at 22° C. 0.19 mmol of the amine and the suspension was stirred for 5 min. A solution of 0.38 mmol of the corresponding benzylbromide in 0.5 ml of DMSO was added slowly keeping the temperature at 15–20° C. and stirring was continued at 22° C. until the conversion was complete. The pH of the reaction mixture was adjusted to 2–3 using formic acid and the product was purified by preparative HPLC chromatography (RP-18, CH$_3$CN/H$_2$O gradient) to give the product as the ester.

The esters were hydrolyzed as described for examples 1–7.

Example 18

Starting from the amine and 2-bromomethyl-3-fluoro-benzoic acid methyl ester, 3-fluoro-2-[({4-[2-(5-methyl-2-phenyl-oxazol-4-yl)-ethoxy]-phenyl}-phenyl-amino)-methyl]-benzoic acid methyl ester was obtained in 55% yield as a pale yellow oil. MS: (M+H)+ 537.3. After hydrolysis, 3-fluoro-2-[({4-[2-(5-methyl-2-phenyl-oxazol-4-yl)-ethoxy]-phenyl}-phenyl-amino)-methyl]-benzoic acid was obtained in 90% yield as a pale brown solid. MS: (M+H)+ 523.1.

Example 19

Starting from the amine and 2-bromomethyl-3-chloro-benzoic acid methyl ester, 3-chloro-2-[({4-[2-(5-methyl-2-phenyl-oxazol-4-yl)-ethoxy]-phenyl}-phenyl-amino)-methyl]-benzoic acid methyl ester was obtained in 43% yield as a pale yellow oil. MS: (M+H)+ 553.1 and 555.3 (Cl isotopes). After hydrolysis, 3-chloro-2-[({4-[2-(5-methyl-2-phenyl-oxazol-4-yl)-ethoxy]-phenyl}-phenyl-amino)-methyl]-benzoic acid was obtained in 74% yield as a colorless solid. MS: (M–H) 537.1 and 539.3 (Cl isotopes).

Example 20

Starting from the amine and 2-bromomethyl-3-trifluoromethyl-benzoic acid methyl ester, 2-[({4-[2-(5-methyl-2-phenyl-oxazol-4-yl)-ethoxy]-phenyl}-phenyl-amino)-methyl]-3-trifluoromethyl-benzoic acid methyl ester was obtained in 59% yield as a colorless oil. MS: (M+H)+ 587.2. After hydrolysis, 2-[({4-[2-(5-methyl-2-phenyl-oxazol-4-yl)-ethoxy]-phenyl}-phenyl-amino)-methyl]-3-trifluoromethyl-benzoic acid was obtained in 87% yield as colorless solid. MS: (M–H) 571.0.

Example 21

Starting from the amine and 2-bromomethyl-3-methoxy benzoic acid methyl ester, 3-methoxy-2-[({4-[2-(5-methyl-2-phenyl-oxazol-4-yl)-ethoxy]-phenyl}-phenyl-amino)-methyl]-benzoic acid methyl ester was obtained in 36% yield as a colorless oil. MS: (M+H)+ 549.2. After hydrolysis, 3-methoxy-2-[({4-[2-(5-methyl-2-phenyl-oxazol-4-yl)-ethoxy]-phenyl}-phenyl-amino)-methyl]-benzoic acid was obtained in 77% yield as a pale yellow solid. MS: (M–H) 533.2.

Example 22

Starting from the amine and 2-bromomethyl-4-chloro-benzoic acid methyl ester, 4-chloro-2-[({4-[2-(5-methyl-2-phenyl-oxazol-4-yl)-ethoxy]-phenyl}-phenyl-amino)-methyl]-benzoic acid methyl ester was obtained in 15% yield as a pale yellow oil. MS: (M+H)+ 553.2 and 555.1 (Cl isotopes). After hydrolysis, 4-chloro-2-[({4-[2-(5-methyl-2-phenyl-oxazol-4-yl)-ethoxy]-phenyl}-phenyl-amino)-methyl]-benzoic acid was obtained in 72% yield as a yellow solid. MS: (M–H) 537.1 and 539.2 (Cl isotopes).

Example 23

Starting from the amine and 2-bromomethyl-4-methoxy-benzoic acid methyl ester, 4-methoxy-2-[({4-[2-(5-methyl-2-phenyl-oxazol-4-yl)-ethoxy]-phenyl}-phenyl-amino)-methyl]-benzoic acid methyl ester was obtained in 14% yield as a colorless oil. MS: (M+H)+ 549.2. After hydrolysis, 4-methoxy-2-[({4-[2-(5-methyl-2-phenyl-oxazol-4-yl)-ethoxy]-phenyl}-phenyl-amino)-methyl]-benzoic acid was obtained in 93% yield as a pale brown solid. MS: (M–H) 533.2.

Example 24

Starting from the amine and 2-bromomethyl-5-fluorobenzoic acid methyl ester, 5-fluoro-2-[({4-[2-(5-methyl-2-phenyl-oxazol-4-yl)-ethoxy]-phenyl}-phenyl-amino)-methyl]-benzoic acid methyl ester was obtained in 44% yield as a colorless oil. MS: (M+H)+ 537.3. After hydrolysis, 5-fluoro-2-[({4-[2-(5-methyl-2-phenyl-oxazol-4-yl)-ethoxy]-phenyl}-phenyl-amino)-methyl]-benzoic acid was obtained in 96% yield as a pale yellow foam. MS: (M–H) 521.1.

Example 25

Starting from the amine and 2-bromomethyl-benzoic acid ethyl ester, 2-[({4-[2-(5-methyl-2-phenyl-oxazol-4-yl)-ethoxy]-phenyl}-phenyl-amino)-methyl]-benzoic acid ethyl ester was obtained in 48% yield as a pale yellow oil. (M+H)+ 533.4. After hydrolysis, 2-[({4-[2-(5-methyl-2-phenyl-oxazol-4-yl)-ethoxy]-phenyl}-phenyl-amino)-methyl]-benzoic acid was obtained in 29% yield as a colorless solid. (M–H) 503.2.

Example 26

Starting from the amine and 2-bromomethyl-6-methoxy-benzoic acid ethyl ester, 2-methoxy-6-[({4-[2-(5-methyl-2-phenyl-oxazol-4-yl)-ethoxy]-phenyl}-phenyl-amino)-methyl]-benzoic acid ethyl ester was obtained in 67% yield as a colorless oil. $(M+H)^+$ 563.3. After hydrolysis, 2-methoxy-6-[({4-[2-(5-methyl-2-phenyl-oxazol-4-yl)-ethoxy]-phenyl}-phenyl-amino)-methyl]-benzoic acid was obtained in 29% yield as a colorless oil. $(M+H)^+$ 535.3.

Example A

Tablets comprising the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules comprising the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:

1. A compound of formula (I):

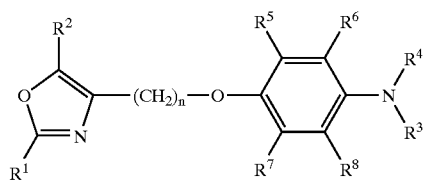

wherein
$R^1$ is aryl;
$R^2$ is hydrogen, alkyl or cycloalkyl;
$R^3$ is hydrogen, alkyl, aralkyl, aryl, alkylcarbonyl, arylcarbonyl, alkyl-$S(O)_2$—, or aryl-$S(O)_2$—;
$R^4$ is aralkyl;
$R_5$, $R^6$, $R^7$ and $R^8$ are independently selected from hydrogen, alkyl or cycloalkyl;
n is 1, 2, 3, 4 or 5;
and pharmaceutically acceptable salts and esters thereof.

2. The compound according to claim 1, wherein $R^1$ is phenyl.

3. The compound according to claim 1; wherein $R^2$ is alkyl.

4. The compound according to claim 3, wherein $R^2$ is methyl.

5. The compound according to claim 1, wherein $R^3$ is alkyl or aryl which is phenyl or phenyl mono- or disubstituted with halogen.

6. The compound according to claim 5, wherein $R^3$ is alkyl which is propyl, or aryl which is phenyl fluorophenyl or difluorophenyl.

7. The compound according to claim 1, wherein $R^4$ is arylmethyl.

8. The compound according to claim 7, wherein $R^4$ is benzyl substituted with carboxy and optionally further substituted with fluoro, chloro, trifluoromethyl or alkoxy.

9. The compound according to claim 1, wherein $R^5$, $R^6$, $R^7$ and $R^8$ are hydrogen.

10. The compound according to claim 1, wherein n is 2.

11. The compound according to claim 1 selected from

2-[({4-(2-(5-Methyl-2-phenyl-oxazol-4-yl)-ethoxy]-phenyl}-phenyl-amino)-methyl]-benzoic acid;

2-[({4-[2-(5-Methyl-2-phenyl-oxazol-4-yl)-ethoxy]-phenyl}-propyl-amino)-methyl]-benzoic acid;

2-[((3-Fluoro-phenyl)-{4-[2-(5-methyl-2-phenyl-oxazol-4-yl)-ethoxy]-phenyl}-amino)-methyl]-benzoic acid;

2-[((3,4-Difluoro-phenyl)-{4-[2-(5-methyl-2-phenyl-oxazol-4-yl)-ethoxy]-phenyl}-amino)-methyl]-benzoic acid;

3-Fluoro-2-[({4-[2-(5-methyl-2-phenyl-oxazol-4-yl)-ethoxy]-phenyl}-phenyl-amino)-methyl]-benzoic acid; and 5-Fluoro-2-[({4-[2-(5-methyl-2-phenyl-oxazol-4-yl)-ethoxy]-phenyl}-phenyl-amino)-methyl]-benzoic acid.

12. A pharmaceutical composition comprising a compound in accordance with claim 1 and a pharmaceutically acceptable carrier.

13. The pharmaceutical composition of claim 12 further comprising a therapeutically effective amount of orlistat.

14. A method for the treatment of non-insulin dependent diabetes mellitus in a patient in need of such treatment, comprising administering to said patient an effective amount of a compound according to claim 1 in amount of from about 1 mg to about 1000 mg per day.

15. The method according to claim 14, wherein the amount administered is from about 1 mg to about 100 mg per day.

16. The method according to claim 14, further comprising administering a therapeutically effective amount of orlistat in an amount of from 60 to 720 mg per day.

17. The method according to claim 16, wherein the compound according to claim 1 and the orlistat are each administered simultaneously, separately or sequentially.

* * * * *